United States Patent [19]

Menon et al.

[11] 4,404,015
[45] Sep. 13, 1983

[54] PREPARATION OF MATERIAL USEFUL AS PLANT NUTRIENTS

[75] Inventors: Kuruvakkat K. G. Menon; Hariharan Raman; Vadali S. Sarma; Bookinkere C. Subba, all of Maharashtra, India

[73] Assignee: Lever Brothers Company, New York, N.Y.

[21] Appl. No.: 281,531

[22] Filed: Jul. 8, 1981

[30] Foreign Application Priority Data

Jul. 18, 1980 [GB] United Kingdom ................ 8023593

[51] Int. Cl.³ ........................................... A01N 27/00
[52] U.S. Cl. .......................................... 71/77; 71/79; 71/122; 71/127; 523/173
[58] Field of Search ................ 260/105, 417; 252/369; 210/638, 702; 523/172; 4/77, 79; 71/122, 127

[56] References Cited

U.S. PATENT DOCUMENTS 2,613,147 10/1952 Owen et al. ............................ 71/26
2,802,844 8/1957 Feuge et al. .
4,150,970 4/1979 Ries et al. .

FOREIGN PATENT DOCUMENTS 398807 of 0000 United Kingdom .
1508304 of 0000 United Kingdom .

OTHER PUBLICATIONS

Principles of Sugar Technology-1953, Honig, pp. 196-207.
Uses of Waste Materials, 1923, Bruttine, p. 326.
"POL Science Data Sheet", No. 199, (Jun. 1977).
"Science", vol. 195, (1977), pp. 1339-1341.
"Chemical Abstracts", vol. 90, p. 186, (1979), (90:116351C).
"Planta", 144, pp. 277-282, (1979).

Primary Examiner—Ferris H. Lander
Attorney, Agent, or Firm—Milton L. Honig; James J. Farrell

[57] ABSTRACT

A plant nutrient composition is obtained by extracting a complex fraction comprising a mixture of water-insoluble long-chain organic compounds from natural plant material, especially from rice bran wax. The fraction is preferably obtained by saponifying rice bran wax and recovering the unsaponifiable residue. The fraction can be employed in dilute aqueous emulsion form as a foliar spray to enhance the growth and yield of many crops, such as rice, wheat and maize, especially in marginal agricultural areas.

9 Claims, No Drawings

PREPARATION OF MATERIAL USEFUL AS PLANT NUTRIENTS

The present invention relates to the preparation of materials useful as plant nutrients.

According to the invention it has been discovered that unsaponifiable material recovered from plants, and particularly from plant waxes, especially rice bran wax, carnauba wax and sugarcane wax, is very effective as a plant nutrient and plant stimulant. It has been found that the unsaponifiable material is most beneficial for increasing yields of a great range of commercial crops, particularly cereals such as rice, wheat and maize, and oil seeds such as sunflower.

The alkaline hydrolysis ("saponification") of oily and waxy materials yields two major fractions- a saponified fraction comprising mainly water-soluble salts of aliphatic acids, and an unsaponified fraction or residue comprising mainly water-insoluble materials including aliphatic alcohols. Each fraction contains a mixture of many components, including a variety of long-chain organic compounds. The compounds in the unsaponified fraction include many typically having carbon chain lengths in the $C_{24}$ to $C_{34}$ range. The detailed composition of each fraction will vary over quite wide limits, due to the natural variation in composition of the starting materials.

The present invention provides a simple and economic way of obtaining an effective plant nutrient composition from natural sources without the need to apply costly purification techniques. The invention is therefore especially suitable for practice in the less well developed areas of the world where there is greatest need for improvements in agriculture and where ideally such improvements are obtained cheaply by exploiting local resources. By applying the invention, highly effective plant nutrient compositions can be extracted from readily-available local materials.

Numerous materials have already been proposed in the literature for use as plant nutrients. Often these are said to require purification before being effective, and even then lead to very inconsistent results when tested. Amongst these materials, the naturally-occuring $C_{30}$ aliphatic alcohol triacontanol has been said to have a stimulating effect on the growth of plants, and purified natural triacontanol has been proposed for use as a plant growth promotor. It has indeed been reported that triacontanol must be free even from trace amounts of other long-chain compounds if it is to be used to increase plant growth. It is possible that triacontanol may be a constituent of a composition of the invention, but the composition will inevitably include major amounts of many other natural long-chain compounds. It is therefore most unexpected that the compositions of the invention are useful as plant nutrients as demonstrated by the field trials described in this specification.

From these field trials it can be seen that use of the invention can lead to very substantial crop yield improvements. These field trials were all conducted in India. The reader will appreciate that the degree of improvement that can be expected will depend to a considerable extent on the local conditions under which crops are grown. In particular, in areas where soils and climate are good, and where relatively advanced agricultural technology and skills are already employed, for example, in temperate areas such as Western Europe, the degree of improvement in percentage terms may be much lower than that attainable in areas where the prevailing agricultural conditions are relatively adverse.

The invention firstly provides a complex fraction derived from plant material, and especially from plant wax, comprising a mixture of unsaponifiable long-chain organic compounds and having a stimulating effect on plants. This fraction will be substantially insoluble in water.

The invention further provides a process for the preparation of a composition having a stimulating effect on plants, wherein plant material, especially plan wax, is fractionated to yield a complex fraction comprising essentially water-insoluble, unsaponifiable matter.

An important embodiment of the invention is a process for the preparation of a composition useful as a plant nutrient, which process comprises saponifying plant material, especially plant wax, to obtain a mixture of saponified and unsaponified material, and recovering the unsaponified material from the mixture.

Most preferably, the composition of the invention is derived from rice bran wax.

Although any alkali can be used to effect the saponification, the saponification is preferably carried out using potassium hydroxide.

Preferably the saponification is carried out in an organic solvent. Preferred organic solvents are toluene, benzene, and lower alkyl alcohols such as methyl alcohol and ethyl alcohol, and mixtures thereof.

Preferably the saponification is carried out under reflux, typically at 80° to 85° C.

The recovery of the unsaponified material from the mixture of saponified and unsaponified material is preferably effected by extraction with an organic solvent, particularly a water-imiscible solvent such as benzene, hexane or petroleum ether, which will dissolve the unsaponified material.

In a further embodiment of the invention the mixture of saponified and unsaponified material is acidified and reduced. This can enhance the yield of useful unsaponified material. Lithium aluminium hydride is particularly preferred as the reducing agent, but other reducing agents commonly known in the art of organic chemistry can be employed. Following reduction, the unsaponified material can be recovered as before.

In a yet further embodiment of the invention, plant material, such as a plant wax, is reduced using a strong reducing agent, and a substantially water-insoluble complex fraction is separated from the reaction mixture. In this alternative process, no true saponification step is employed, but the substantially water-insoluble fraction can in practice be equated with the unsaponifiable fraction in terms of its general composition and growth-promoting properties.

The recovered unsaponifiable material of the invention is itself useful as a plant nutrient and plant stimulant and can be employed directly as such. However, in order to make it convenient to apply small quantities of the material to large areas of crop and to ensure that the material is easily and rapidly taken up by the plants, the recovered unsaponifiable material is preferably applied as a dilute aqueous composition, such as foliar spray composition.

An important further embodiment of the invention provides a method for preparing a plant treatment composition which method comprises bringing into intimate contact recovered unsaponifiable material, obtained as hereinbefore described, with water in the presence of one or more emulsifying agents.

The emulsion is preferably initially prepared in the form of a concentrate, which can then be diluted as necessary with water before being physically applied to plants or to the soil.

The quantity of the recovered unsaponifiable material in the diluted composition applied to plants or soil is preferably from 0.01 to 5 ppm, and most preferably from 0.1 to 1 ppm.

The emulsifier will generally be of the anionic or non-ionic type. Examples of suitable anionic emulsifiers are fatty acid soaps, alkyl and alkyl aryl sulphonates, alcohol sulphonates and phosphate esters. Examples of suitable non-ionic emulsifiers are glycerol esters and sorbitan esters, ethoxylated derivatives of these esters, ethoxylated alcohols and polyethylene and glycol esters. Mixtures of anionic and non-ionic emulsifiers can be employed. Most preferably the commercially available emulsifying agents ethoxylated cetyl/oleyl alcohol and phosphated cetyl/oleyl alcohol are used.

Preferably a thickening or suspending agent is added to the emulsion to ensure good stability. Suitable agents include, for example, guar gum and sodium carboxymethyl cellulose.

In a further embodiment of the invention, the recovered unsaponifiable material is used as a treatment for seeds. Preferably, the seeds are soaked in an aqueous emulsion of the unsaponified material prior to planting. This treatment can significantly increase the growth of the root system in the germinating seed. Alternative manners of application are as a root dip prior to replanting, or as a soil treatment prior to or following seeding or planting.

Various aspects of the invention are illustrated in the following examples.

A. Preparation of a basic plant wax:

Samples of raw rice bran oil, received from various parts of India, were centrifuged after cooling. The supernatent oil in each case was removed and the solid portion was washed with cold organic solvents such as ether or hexane, followed by washing with an acetone/isopropyl alcohol mixture.

The partially refined wax thus obtained was then dried, and analytical parameters were determined on individual individual samples. The particulars of two samples are given in Table 1.

TABLE 1

| | Analytical data on partially refined rice bran wax | | | | | |
|---|---|---|---|---|---|---|
| No. | Source | Yield ex Oil (w/w %) | M.P. °C. | I.V. | A.V. | Sap Value | Unsap. % |
| 1. | Hyderabad | 1.06 | 80 | 21.7 | 1.2 | 109.4 | 59.6 |
| 2. | Calcutta | 0.40 | 79 | 27.8 | 0.5 | 107.9 | 56.0 |

B. Preparation of the unsaponified material of the invention

The details of typical procedures employed for the preparation of the unsaponified material are given in Examples 1 to 3.

EXAMPLE 1

Crude rice bran wax (5 g) was taken up in a mixture of benzene (13 ml) and aqueous ethanol (13% v/v of water, 113 ml). Potassium hydroxide (20 g) was added, and the mixture was refluxed for about 3 hours. The solvents were distilled off and the reaction mixture was extracted with benzene (2×100 ml). The benzene solution was washed with water and dried over sodium sulphate. Evaporation of the benzene yielded 2.7 g of unsaponified material.

EXAMPLE 2

Crude rice bran wax (60 g) was taken up in a 3 liter three-necked, round-bottomed flask, fitted with a mechanical stirrer, a water condenser and thermometer. Benzene (150 ml), potassium hydroxide (218 g) and water (150 ml) were added, followed by ethanol (1200 ml). The mixture was refluxed during stirring for 8 hours. After the reaction period, the solvents were distilled off. The residue was boiled with water (1.5 liters) and was transferred to a 3 liter beaker. Sodium chloride was added and the mixture boiled to grain the solid product. The product was filtered through a muslin cloth. The residue was again treated with aqueous sodium chloride in the same manner twice, until the pH was about 7–8. The solid product was dried at about 60° C. for 24 hours and then taken for soxhlet extraction using petroleum-ether (60°–80°, 2 liters). Evaporation of solvents yielded crude unsaponified material as a solid, 24 g (40% w/w), m.p. 80°–82° C., OH value (on different batches) = 120–134, IR: 3100–3500 cm$^{-1}$ (—OH) (no ester group). NMR (CCl$_4$: in ppm): 1.23 (—CH$_2$); 0.9 (—CH$_3$).

EXAMPLE 3

Crude rice bran wax (60 g) was taken up in a 500 ml three-necked, round-bottomed flask, fitted with a mechanical stirrer, a water condenser and thermometer. Benzene (10.5 ml), potassium hydroxide (15 g) and water (10.5 ml) were added, followed by ethanol (82.5 ml). The mixture was refluxed during 2 hours. After the reaction period was over, the solvents were distilled off. The residue was boiled with water (1 liter) and was transferred to a 3 liter beaker. Sodium chloride was added and the mixture was boiled to grain the solid product. The product was filtered through a muslin cloth. The residue was again treated with aqueous sodium chloride in the same manner until the pH of the washings was about 7–8. The material was dried in an oven at 100°–110° C. for 6 hours. It was ground and taken for soxhlet extraction using hexane (1 liter). Evaporation of solvents gave crude unsaponified matter; yield 25.6 g (42.7% w/w), mp 80°–85° C., OH value (on different batches) 110–120, IR: 3100–3500 cm$^{-1}$ (OH); no ester group.

C. Plant treatment compositions

Some examples (Nos. 4 to 9) of concentrated emulsions, that were used in diluted form in plant trials, are given in Table 2. In the details of the plant trials, references to concentrations (in ppm) refer to actual concentrations of the unsaponifiable material of the invention present in the dilute foliar sprays or other dilute treatments.

TABLE 2

| | Details of undiluted compositions | | | | | |
|---|---|---|---|---|---|---|
| Ingredient | Example No. | | | | | |
| (% by weight) | 4 | 5 | 6 | 7 | 8 | 9 |
| Unsaponified material ex rice bran wax | 0.1 | 1.0 | 0.5 | 1.0 | 0.5 | 1.0 |
| Ethoxylated cetyl/ oleyl alcohol | 0.1 | 1.0 | 1.0 | — | 1.0 | — |

TABLE 2-continued

Details of undiluted compositions

| Ingredient | Example No. | | | | | |
|---|---|---|---|---|---|---|
| (% by weight) | 4 | 5 | 6 | 7 | 8 | 9 |
| Phosphate ester of ethoxylated cetyl/oleyl alcohol | 0.1 | 1.0 | — | — | — | — |
| Glycerol monostearate | — | — | 1.5 | — | — | — |
| "Tween 40" | — | — | — | 1.0 | — | 1.0 |
| "Tween 80" | — | — | — | 1.0 | — | 1.0 |
| Guar Gum | — | — | — | — | 0.5 | 0.5 |
| Water | to 100.0 | | | | | |

D. Testing of foliar spray compositions

Foliar spray compositions of the invention were tested for stimulation of growth of plants and yield of plant products in agricultural field experiments on a pot scale (in Bombay), small scale (also in Bombay) and large scale (in Bombay as well as Etah) and the results are given below. The plants and crops tested were maize, sunflower, rice and wheat.

Various dilutions of an emulsion as per Example 4 above were applied on maize and rice plants in pots by single foliar spraying on 15 days old plants. The effect was compared with plants which were sprayed with only the control solution of emulsifier in corresponding concentrations; or with plants not sprayed at all.

The test solutions were also applied by 3 foliar sprayings at weekly intervals on 35 day old plants of sunflower and maize in the field and the results compared with equal number of plants sprayed with similar concentrations of blank solution.

(i) Pot Experiments (Bombay)

(a) Maize:

12 plants sprayed with 0.1 ppm test solution;
6 plants sprayed with control solution.

| Increase in wt. of cobs | Increase in No. of seeds | Increase in wt. of seeds |
|---|---|---|
| 50% | 70% | 70% |

(b) Rice:

30 plants sprayed with 0.1 ppm test solution;
15 plants not sprayed.
Increase in dry weight of plants ... 59%

(ii) Small scale field experiments (Bombay)

| | Increase in Yield | Increase in Dry wt. |
|---|---|---|
| (a) Sunflower (var. Morden) | | |
| 115 plants sprayed with test solution; equal No. sprayed with control solution. | 30% | 22% |
| (b) Maize | | |
| 20 plants sprayed with test solution; 20 plants control | 11% | 4% |

(iii) Large scale field experiments

(a) Bombay:

About 2-month old seedlings of rice, varieties Karjat and Jaya, were foliar sprayed at 3 concentrations, vix., 0.01, 0.1 and 1.00 ppm dilutions of the composition as per Example 5 above, containing the unsaponified material thrice at 15 day intervals. The control plants were either unsprayed or sprayed with corresponding concentrations of the emulsifier in water. The seven treatments were replicated four times. The treatments were allocated by statistically randomised design. Data on height at different time intervals, grain and fodder yields per bed, number of fertile and sterile tillers from 10 randomly selected plants from each bed were statistically analysed. Control solutions did not contain the unsaponified material of the invention. Data on grain yield are given in Table 3.

TABLE 3

| Conc. of unsap-onified material in spray solution | Rice Yield (kg) | | | | | |
|---|---|---|---|---|---|---|
| | Variety: Karjat | | | Variety: Jaya | | |
| | Exptl. | Control | % Increase | Exptl. | Control | % increase |
| 1.00 ppm | 18.55 | 15.90 | 16 | 12.20 | 18.03 | 29 |
| 0.1 ppm | 20.25 | 16.15 | 22 | 21.83 | 19.80 | 10 |
| 0.01 ppm | 19.75 | 16.90 | 14 | 21.30 | 20.65 | 3 |
| Overall yield | | | 17 | | | 14 |

In var. Karjat, the grain yields due to the treatment were higher by 14, 16 and 22 percent, in the 3 groups, giving an overall increase of 17 percent over corresponding groups treated with the blank emulsion and 12.4 percent over the untreated control. The fodder increase range from 2 to 10 percent with an overall increase of 7 percent over blank emulsion and 3 percent over untreated control.

In var. Jaya, in the replicated trials, grain yields due to the treatment were higher by 3, 10 and 29 percent in the three groups giving an overall increase of 14 percent over groups sprayed with blank emulsion, and 3 percent over the untreated control. The increase in fodder weight by 1.6, 6.25 and 23.3 percent giving an overall increase of about 10 percent.

In another experiment, 3 plots (300, 500, 600 sq.m.) divided into 4 or 6 strip beds, alternate beds were unsprayed or sprayed with test material at 0.01 ppm concentration. Thus plants on a total area of 700 sq.m. were sprayed and on an equivalent area, unsprayed. Results are given in Table 4.

Rice plants, var. Jaya sprayed with 0.01 ppm of the test material on the 3 large plots gave increase in grain yields 12, 18 and 23 percent or an overall increase of 18 percent over that from unsprayed plants.

(b) Etah:

Rice experiments carried out as above on 3 rice varieties, viz., Jaya, Basmati and Lakra gave the following results:
Var. Jaya—12% increase in grain yield. 15% increase in fodder yield.
Var. Basmati—15% increase in grain yield.
Var. Lakra—8–11% increase in grain yield.

(c) Andhra Pradesh:

In the summer of 1979, field trials were conducted with the co-operation of five farmers on more than 1 hectare of land each in the rice growing region of Nizamabad, Andhra Pradesh.

TABLE 4

Further Trials with Rice Variety, Jaya in Bombay

| | Area sq. m. | | Grain Yields | | | | Percent increase of treated over control |
|---|---|---|---|---|---|---|---|
| | | | Control (not sprayed) | | Treated 0.01 ppm Exptl. Solution | | |
| Plot | Control | Treated | kg/plot | Est. yields kg/ha. | kg/plot | Est. yields kg/ha. | |
| A | 250 | 250 | 82 | 3280 | 92 | 3680 | 12 |
| B | 300 | 300 | 86 | 2870 | 106 | 3530 | 23 |
| C | 150 | 150 | 38 | 2533 | 45 | 3000 | 18 |

The farmers in this region are progressive and adopt the best management practices. The application of foliar sprays containing 1 ppm of the rice bran wax fraction of the invention (dilution of concentrate as per Example 7 above) was able to increase grain yields ranging from 400 to 800 kg per hectare.

In the Kharis season of 1979, field trials were carried out in another 4 regions of Andhra Pradesh, viz., Hyderabad, Warangal, Kurnool and Nandyal on the fields of 28 farmers with 12 different varieties of rice. These trials confirmed earlier results and gave a mean increase of 880 kg per hectare or 27 percent over control crops.

Further extension trials on rice during the summer of 1980 in the fields of 18 farmers in Andhra Pradesh once again confirmed the beneficial effect of the material of the invention on crops, and gave mean increases in grain yields of 750 kg per hectare or 21 percent over control.

Wheat

Field trials on large scale were carried out on wheat at Etah in 1979 Rabi Season, i.e. December 1979 to April 1980. Five farms were chosen. Half the area in each farm was sprayed with 1 ppm of spraying composition containing the material of the invention (as per Example 7 above) while the other half was used as control. Spraying was done twice, first time after 30 days after sowing and second time after 60 days of sowing. The grain yields in each of the farms are shown in Table 5, together with the increases in grain yield in the sprayed part of the fields.

TABLE 5

Results of Wheat growing trials at Etah

| Farm No. | Total Area (Sq. m.) | Grain Yield (kg/ha) | | Increase in grain Yield | |
|---|---|---|---|---|---|
| | | Control | Sprayed | kg/ha | % |
| 1 | 360 | 3333 | 4388 | 1055 | 32 |
| 2 | 1064 | 2250 | 3100 | 850 | 38 |
| 3 | 2800 | 2640 | 3130 | 490 | 19 |
| 4 | 1800 | 2770 | 4220 | 1450 | 52 |
| 5 | 554 | 1010 | 1510 | 500 | 50 |

The increase in yield of wheat by 2 sprays of 1 ppm of spraying composition containing the material of the invention ranged between 500 to 1450 kg/ha.

E. Results of seed-soak treatment before sowing

The seeds were: Sorghum, rice and wheat. The seeds were soaked for 24 hours in (a) distilled water (control), (b) composition containing 1 ppm dilution of the concentrate of Example 7 in distilled water, and, (c) blank emulsion (without the unsaponified material of the invention) prepared with distilled water.

Of the seeds of each species 100 were soaked in 25 ml of liquid (a), 100 in liquid (b) and 100 in liquid (c). The seeds were germinated on moist filter paper in petri-dish. On germination 15 seeds each from the three groups soaked in liquids (a), (b) and (c) were sown in pots; one seed in one pot. The plants were given identical treatment for three weeks.

The growth parameters were recorded at weekly intervals. The results (average of 5 plants) at the end of 3 weeks are given in Table 6.

The experiment illustrated that as a result of the seed treatment there was a significant gain in the growth of the plant in three weeks.

EXAMPLE 10

In a 500 ml flat-bottomed flask, lithium aluminium hydride ($LiAlH_4$) (2.2 g) mixed with 150 ml of dry tetra-hydrofuran (THF) and stirred for 1 hour at room temperature. At the end of 1 hour, rice bran wax (5 g) in 100 ml of warm THF was added slowly. After the addition, the mixture was stirred for 1 hour at room temperature and then it was refluxed for 5½ hours. The excess $LiAlH_4$ was destroyed with ethylacetate (50 ml) and then with wet ethylacetate (25 ml) after cooling the contents with ice. The grey coloured material was removed with 100 ml of 5% NaOH. Then it was filtered and washed with water (500 ml) to neutrality. Finally, the material was mixed with 300 ml of water and boiled, and then the material was grained with NaCl (30 gms). The weight of dried material obtained was 3.78 gms. IR analysis showed the absence of ester carbonyl, indicating complete reduction of ester to alcohol. Hydroxyl value: 128.

This material also exhibited valuable nutrient properties when applied to plants in accordance with the invention.

TABLE 6

Results of Seed Soak Treatment

| | Height (cm) | | | No. of leaves | | | Leaf Area (sq. cm) | | | Total Plant Weight (gm) | | | | | |
|---|---|---|---|---|---|---|---|---|---|---|---|---|---|---|---|
| | | | | | | | | | | Fresh | | | Dry | | |
| | (a) | (b) | (c) | (a) | (b) | (c) | (a) | (b) | (c) | (a) | (b) | (c) | (a) | (b) | (c) |
| Sorghum | 24 | 40 | 24 | 5 | 7 | 4 | 51 | 156 | 61 | 4 | 18 | 5 | 0.7 | 2.4 | 0.7 |
| Rice | 16 | 25 | 16 | 5 | 6 | 5 | 9 | 23 | 10 | 0.8 | 1.7 | 1 | 0.2 | 0.5 | 0.2 |
| Wheat | 18 | 26 | 21 | 6 | 11 | 7 | 18 | 56 | 27 | 2.2 | 5.4 | 2.8 | 0.3 | 1.0 | 0.4 |

What is claimed is:

1. A process for the preparation of an aqueous composition useful as a plant growth stimulant, which process comprises the steps of:
   (a) saponifying a plant wax selected from the group consisting of rice bran wax and carnauba wax to obtain a mixture of saponified and unsaponified material;
   (b) recovering unsaponified material from the mixture by extraction with a water-immiscible organic solvent; and
   (c) mixing the recovered unsaponified material with water and one or more emulsifying agents.

2. A process for the preparation of an aqueous composition, useful as a plant growth stimulant which process comprises the steps of:
   (a) reducing plant wax using a strong reducing agent; and
   (b) separating a substantially water-insoluble fraction from the reaction mixture, said substantially water-insoluble fraction consisting essentially of a mixture of unsaponifiable long-chain organic compounds; and
   (c) mixing said fraction with water and one or more emulsifying agents.

3. A process for the preparation of a material useful as a plant growth stimulant which process comprises the steps of:
   (a) saponifying rice bran wax or carnauba wax under reflux in the presence of an organic solvent, to yield a mixture of saponified and unsaponified material; and
   (b) extracting from said mixture a complex fraction consisting essentially of unsaponifiable long-chain organic compounds.

4. A method for promoting the growth of plants, in which method said plants are treated with an aqueous composition comprising:
   (a) water;
   (b) an emulsifying agent; and
   (c) a complex fraction, in about 0.01 to 5 ppm by weight of the final compositions derived from saponifying rice bran wax, sugarcane wax or carnauba wax to yield a mixture of saponified and unsaponified material, and extracting from said mixture a complex fraction consisting essentially of unsaponifiable long-chain organic compounds.

5. A method for promoting the growth of plants, in accordance with claim 4 wherein the plants are treated by foliar spraying.

6. A method for promoting the growth of plants, in accordance with claim 4 wherein the plants are treated by root dipping.

7. A method for promoting the growth of plants comprising treating the seeds of said plants with an aqueous composition comprising:
   (a) water;
   (b) an emulsifying agent; and
   (c) a complex fraction, in about 0.01 to 5 ppm by weight of the final composition, derived from saponifying rice bran wax, sugarcane wax or carnauba wax to yield a mixture of saponified and unsaponified material, and extracting from said mixture a complex fraction consisting essentially of unsaponifiable long-chain organic compounds.

8. A method for promoting the growth of plants comprising treating the soil prior to planting with an aqueous composition comprising:
   (a) water;
   (b) an emulsifying agent; and
   (c) a complex fraction, in about 0.01 to 5 ppm by weight of the final composition, derived from saponifying rice bran wax, sugarcane wax or carnauba wax to yield a mixture of saponified and unsaponified material, and extracting from said mixture a complex fraction consisting essentially of unsaponifiable long-chain organic compounds.

9. A method for promoting the growth of plants comprising treating said plants or their seeds or the soil in which said plants will be planted with an aqueous composition comprising:
   (a) water;
   (b) an emulsifying agent; and
   (c) a complex fraction, in about 0.01 to 5 ppm by weight of the final composition, derived from saponifying plant wax to yield a mixture of saponified and unsaponified material, and extracting from said mixture said complex fraction consisting essentially of unsaponifiable long-chain organic compounds.

* * * * *